(12) United States Patent
Stadler et al.

(10) Patent No.: US 11,801,390 B2
(45) Date of Patent: Oct. 31, 2023

(54) IDENTIFICATION AND ADJUSTMENT FOR LOSS OF EFFECTIVE CARDIAC RESYNCHRONIZATION THERAPY

(71) Applicant: Medtronic, Inc., Minneapolis, MN (US)

(72) Inventors: Robert W. Stadler, Shoreview, MN (US); Ruth N. Klepfer, St. Louis Park, MN (US); Subham Ghosh, Blaine, MN (US); Yanina Grinberg, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 571 days.

(21) Appl. No.: 16/001,453

(22) Filed: Jun. 6, 2018

(65) Prior Publication Data
US 2019/0374781 A1    Dec. 12, 2019

(51) Int. Cl.
| | | |
|---|---|---|
| A61N 1/372 | (2006.01) | |
| A61N 1/365 | (2006.01) | |
| A61B 5/00 | (2006.01) | |
| A61N 1/368 | (2006.01) | |

(52) U.S. Cl.
CPC ..... *A61N 1/37252* (2013.01); *A61N 1/36585* (2013.01); *A61B 5/721* (2013.01); *A61N 1/368* (2013.01); *A61N 1/36542* (2013.01)

(58) Field of Classification Search
CPC .............................. A61N 1/371; A61N 1/3712
See application file for complete search history.

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,955,376 A | 9/1990 | Callaghan et al. |
| 5,052,388 A | 10/1991 | Sivula et al. |
| 5,324,310 A | 6/1994 | Greeninger et al. |
| 5,411,524 A | 5/1995 | Rahul |
| 5,443,492 A | 8/1995 | Stokes et al. |

(Continued)

FOREIGN PATENT DOCUMENTS

EP    1110580 A2    6/2001

OTHER PUBLICATIONS (PCT/US2019/035721) PCT Notification of Transmittal of the International Search Report and the Written Opinion of the International Searching Authority, dated Sep. 19, 2019, 13 pages.

(Continued)

*Primary Examiner* — Allen Porter
(74) *Attorney, Agent, or Firm* — Mueting Raasch Group

(57) ABSTRACT

An implantable medical device system and method for delivering cardiac resynchronization therapy (CRT) pacing that includes determining capture associated with the delivered CRT pacing is ineffective in response to the delivered CRT pacing. A reason for capture being ineffective is determined and a safety margin is adjusted if the determined reason for capture being ineffective is loss of capture and a left ventricle (LV) pre-excitation is adjusted if the determined reason for capture being ineffective is delayed LV depolarization. Monitoring for a change in effective cardiac resynchronization therapy is used to confirm that the adjustment of the CRT pacing was effective in resolving the ineffective capture.

23 Claims, 10 Drawing Sheets

(56) References Cited

U.S. PATENT DOCUMENTS

| | | |
|---|---|---|
| 5,628,778 A | 5/1997 | Kruse et al. |
| 5,766,230 A | 6/1998 | Routh et al. |
| 5,922,014 A | 7/1999 | Warman et al. |
| 5,954,756 A | 9/1999 | Hemming et al. |
| 5,999,850 A | 12/1999 | Dawson et al. |
| 6,643,549 B1 | 11/2003 | Bradley et al. |
| 6,704,598 B2 | 3/2004 | Ding et al. |
| 6,804,555 B2 | 10/2004 | Warkentin |
| 6,871,096 B2 | 3/2005 | Hill |
| 6,968,237 B2 | 11/2005 | Doan et al. |
| 7,031,777 B2 | 4/2006 | Hine et al. |
| 7,123,963 B2 | 10/2006 | Sawchuk et al. |
| 7,139,610 B2 | 11/2006 | Ferek-Petric |
| 7,181,284 B2 | 2/2007 | Burnes et al. |
| 7,187,972 B1 | 3/2007 | Fain et al. |
| 7,254,442 B2 | 8/2007 | Van Gelder et al. |
| 7,313,444 B2 | 12/2007 | Pianca et al. |
| 7,424,323 B1 | 9/2008 | Reiss et al. |
| 7,515,959 B2 | 4/2009 | Hess |
| 7,684,863 B2 | 3/2010 | Parikh et al. |
| 7,715,917 B2 | 5/2010 | Chinchoy et al. |
| 7,831,303 B2 | 11/2010 | Rueter et al. |
| 7,848,807 B2 | 12/2010 | Wang |
| 7,860,580 B2 | 12/2010 | Falk et al. |
| 7,881,787 B1 | 2/2011 | Min et al. |
| 7,908,004 B1 | 3/2011 | Gill et al. |
| 7,917,214 B1 | 3/2011 | Gill et al. |
| 7,920,920 B1 | 4/2011 | Williamson |
| 7,953,482 B2 | 5/2011 | Hess |
| 7,970,473 B2 | 6/2011 | Nabutovsky et al. |
| 8,036,743 B2 | 10/2011 | Savage et al. |
| 8,046,065 B2 | 10/2011 | Burnes et al. |
| 8,145,308 B2 | 3/2012 | Sambelashvili et al. |
| 8,160,700 B1 | 4/2012 | Ryu et al. |
| 8,271,087 B2 | 9/2012 | Sathaye et al. |
| 8,489,188 B2 | 7/2013 | Giorgis et al. |
| 8,615,298 B2 | 12/2013 | Ghosh et al. |
| 8,620,433 B2 | 12/2013 | Ghosh et al. |
| 8,738,132 B1 | 5/2014 | Ghosh et al. |
| 8,750,998 B1 | 6/2014 | Ghosh et al. |
| 8,750,999 B1 | 6/2014 | Ghosh et al. |
| 8,929,984 B2 | 1/2015 | Ghosh et al. |
| 9,320,905 B2 | 4/2016 | Ghosh et al. |
| 9,604,064 B2 | 3/2017 | Ghosh et al. |
| 2004/0116974 A1 | 6/2004 | Obel |
| 2004/0215259 A1 | 10/2004 | Krig et al. |
| 2006/0155338 A1 | 7/2006 | Mongeon et al. |
| 2006/0235478 A1 | 10/2006 | Van Gelder et al. |
| 2006/0293717 A1 | 12/2006 | Sathaye et al. |
| 2009/0036947 A1 | 2/2009 | Westlund et al. |
| 2009/0270729 A1 | 10/2009 | Corbucci et al. |
| 2009/0276001 A1 | 11/2009 | Busacker et al. |
| 2010/0016914 A1 | 1/2010 | Mullen et al. |
| 2010/0057156 A1 | 3/2010 | Chow |
| 2010/0100148 A1* | 4/2010 | Min .................. A61N 1/3712 607/27 |
| 2010/0121397 A1 | 5/2010 | Cholette |
| 2010/0137935 A1 | 6/2010 | Parikh et al. |
| 2010/0262204 A1 | 10/2010 | McCabe et al. |
| 2011/0054559 A1 | 3/2011 | Rosenberg et al. |
| 2011/0054560 A1 | 3/2011 | Rosenberg et al. |
| 2011/0066201 A1 | 3/2011 | Rosenberg et al. |
| 2011/0098772 A1 | 4/2011 | Min |
| 2011/0137369 A1 | 6/2011 | Ryu et al. |
| 2011/0172728 A1 | 7/2011 | Wang |
| 2011/0319951 A1 | 12/2011 | More et al. |
| 2012/0165897 A1 | 6/2012 | Enrooth |
| 2012/0191154 A1 | 7/2012 | Ryu et al. |
| 2012/0239116 A1 | 9/2012 | Lee |
| 2013/0090702 A1 | 4/2013 | Mongeon et al. |
| 2013/0190834 A1 | 7/2013 | Ghosh et al. |
| 2013/0218223 A1 | 8/2013 | Ghosh et al. |
| 2013/0218224 A1 | 8/2013 | Ghosh et al. |
| 2013/0218225 A1 | 8/2013 | Ghosh et al. |
| 2013/0218226 A1 | 8/2013 | Ghosh et al. |
| 2013/0218227 A1 | 8/2013 | Ghosh et al. |
| 2014/0163633 A1 | 6/2014 | Ghosh et al. |
| 2014/0180355 A1 | 6/2014 | Ghosh et al. |
| 2014/0277245 A1 | 9/2014 | Lu et al. |
| 2014/0277246 A1 | 9/2014 | Lu et al. |
| 2015/0246235 A1* | 9/2015 | Ghosh .................. A61N 1/3712 607/28 |

OTHER PUBLICATIONS

U.S. Appl. No. 61/580,058, filed Dec. 23, 2011, Ghosh et al..
(PCT/US2014/028108) PCT Notification of Transmittal of the International Search Report and the Written Opinion of the International Searching Authority; 12 pages.
(PCT/US2013/072974) PCT Notification of Transmittal of the International Search Report and the Written Opinion of the International Searching Authority; dated Nov. 14.

* cited by examiner

IDENTIFICATION AND ADJUSTMENT FOR LOSS OF EFFECTIVE CARDIAC RESYNCHRONIZATION THERAPY

The disclosure herein relates to systems and methods for delivery of cardiac pacing therapy, and, more particularly, to delivery of cardiac resynchronization therapy.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Cardiac resynchronization pacing devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. Delivering electrical stimuli that causes the ventricle to respond is commonly referred to as capturing a ventricle. For a variety of reasons, cardiac pacing systems may not achieve effective capture of a ventricle. For example, a pacing lead and/or electrode may not be placed in an optimal location. Sensed atrioventricular delay (SAV), paced atrioventricular delay (PAV), right ventricular pre-excitation may also affect whether a ventricle is effectively captured. Additionally, after the medical device has been implanted, migration or dislodgement of the pacing lead may occur.

SUMMARY

The exemplary systems, methods, and interfaces described herein may be configured to a medical device system and method for delivering cardiac resynchronization therapy (CRT) pacing to a patient. Delivery of the CRT pacing is monitored to determine whether the CRT pacing is effectively capturing the patient's heart. During episodes of loss of effective capture a reason for the loss of capture is determined and adjustments to the CRT pacing are automatically made if the user has given the device permission to make automatic changes, i.e., automatic changes have been enabled. For example, when the reason for ineffective capture is determined to be loss of capture, the safety margin associated with the delivered pacing may be increased, and if increasing the safety margin does not resolve the ineffective capture, a determination may be made as to whether there is a very low percentage effective CRT. If a low percentage effective CRT is determined, the delivery of the pacing may be switched to a minimum ventricular pacing mode and an alarm may be generated. If the left ventricular capture management feature is not enabled, no changes are made to the pacing, but rather, an alarm or observation of the event is generated.

When the reason for ineffective capture are is determined to be delay left ventricular depolarization (i.e., resulting from the lead being positioned within scar tissue or within latent or inactive tissue), left ventricular pre-excitation may be increased. If increasing of the LV pre-excitation does not resolve the ineffective capture, the LV pre-excitation is adjusted back to a baseline LV pre-excitation, and a vector for delivery the pacing is adjusted if a vector adjustment feature is enabled. If adjusting of the vector does not resolve the ineffective capture, a determination may be made as to whether there is a very low percentage effective CRT. If a low percentage effective CRT is determined, the delivery of the pacing may be switched to a minimum ventricular pacing mode and an alarm may be generated.

In one example, the exemplary systems and methods can include an implantable medical device system for delivering cardiac resynchronization therapy (CRT) pacing, comprising: an implantable medical device housing; at least one lead having a lead body and capable of being electrically coupled to the housing; a plurality of electrodes positioned along one or both of the device housing and the lead body of the at least one lead to sense a cardiac signal of the patient and to deliver the CRT pacing; and a processor positioned within the housing and configured to determine capture associated with the delivered CRT pacing is ineffective in response to the delivered CRT pacing, determine a reason for capture being ineffective, and adjust a safety margin in response to the determined reason for capture being ineffective being loss of capture and adjusting a left ventricle (LV) pre-excitation in response to the determined reason for capture being ineffective being delayed LV depolarization.

In at least one example, a method of delivering cardiac resynchronization therapy (CRT) pacing, comprises: determining capture associated with the delivered CRT pacing is ineffective in response to the delivered CRT pacing; determining a reason for capture being ineffective; and adjusting a safety margin in response to the determined reason for capture being ineffective being loss of capture and adjusting a left ventricle (LV) pre-excitation in response to the determined reason for capture being ineffective being delayed LV depolarization.

In another example, example, a non-transitory computer readable medium storing instructions which cause an implantable medical device to perform a method, the method comprising: determining capture associated with the delivered CRT pacing is ineffective in response to the delivered CRT pacing; determining a reason for capture being ineffective; and adjusting a safety margin in response to the determined reason for capture being ineffective being loss of capture and adjusting a left ventricle (LV) pre-excitation in response to the determined reason for capture being ineffective being delayed LV depolarization.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
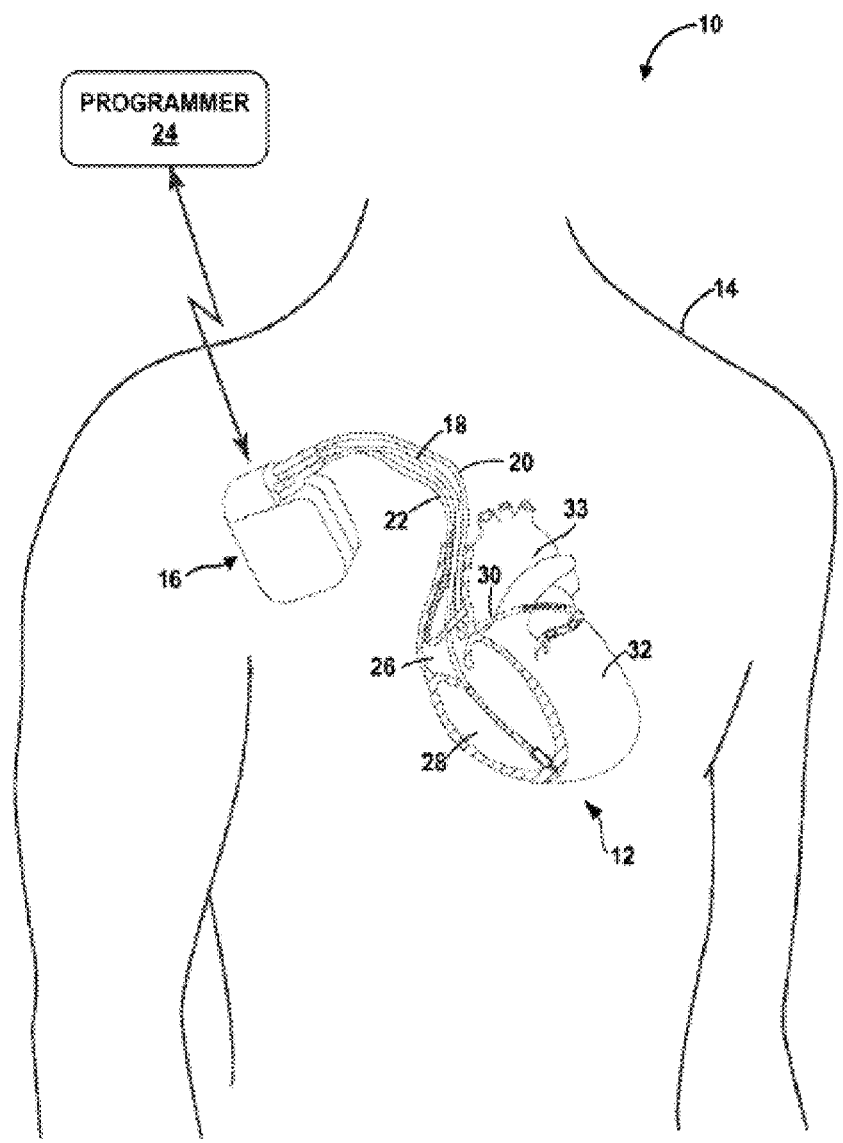
FIG. 1 is a conceptual diagram illustrating an exemplary therapy system including an exemplary implantable medical device (IMD) that may be used to deliver pacing therapy to a patient according to an embodiment of the present disclosure.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-8. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Various exemplary systems, methods, and interfaces described herein may be configured to a medical device system and method for delivering cardiac resynchronization therapy (CRT) pacing to a patient. Delivery of the CRT pacing is monitored to determine whether the CRT pacing is effectively capturing the patient's heart. During episodes of loss of effective capture, a reason for the loss of capture is determined and adjustments to the CRT pacing are automatically made if a capture management feature has been enabled. For example, when the reason for ineffective capture is determined to be loss of capture, the pacing output (amplitude, pulse width or both) may be increased. In another example, the safety margin associated with the delivered pacing may be increased. If neither increasing the pacing output or increasing the safety margin resolve the ineffective capture, a determination may be made as to whether there is a very low percentage effective CRT. If a low percentage effective CRT is determined, the delivery of the pacing may be switched to a minimum ventricular pacing mode and an alarm may be generated. If the left ventricular capture management feature is not enabled, no changes are made to the pacing, but rather, an alarm or observation of the event is generated.

When the reason for ineffective capture are is determined to be delay left ventricular depolarization (i.e., resulting from the lead being positioned within scar tissue or within latent or inactive tissue), left ventricular pre-excitation may be increased. If increasing of the LV pre-excitation does not resolve the ineffective capture, the LV pre-excitation is adjusted back to a baseline LV pre-excitation, and a vector for delivery the pacing is adjusted if a vector adjustment feature is enabled. If adjusting of the vector does not resolve the ineffective capture, a determination may be made as to whether there is a very low percentage effective CRT. If a low percentage effective CRT is determined, the delivery of the pacing may be switched to a minimum ventricular pacing mode and an alarm may be generated.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
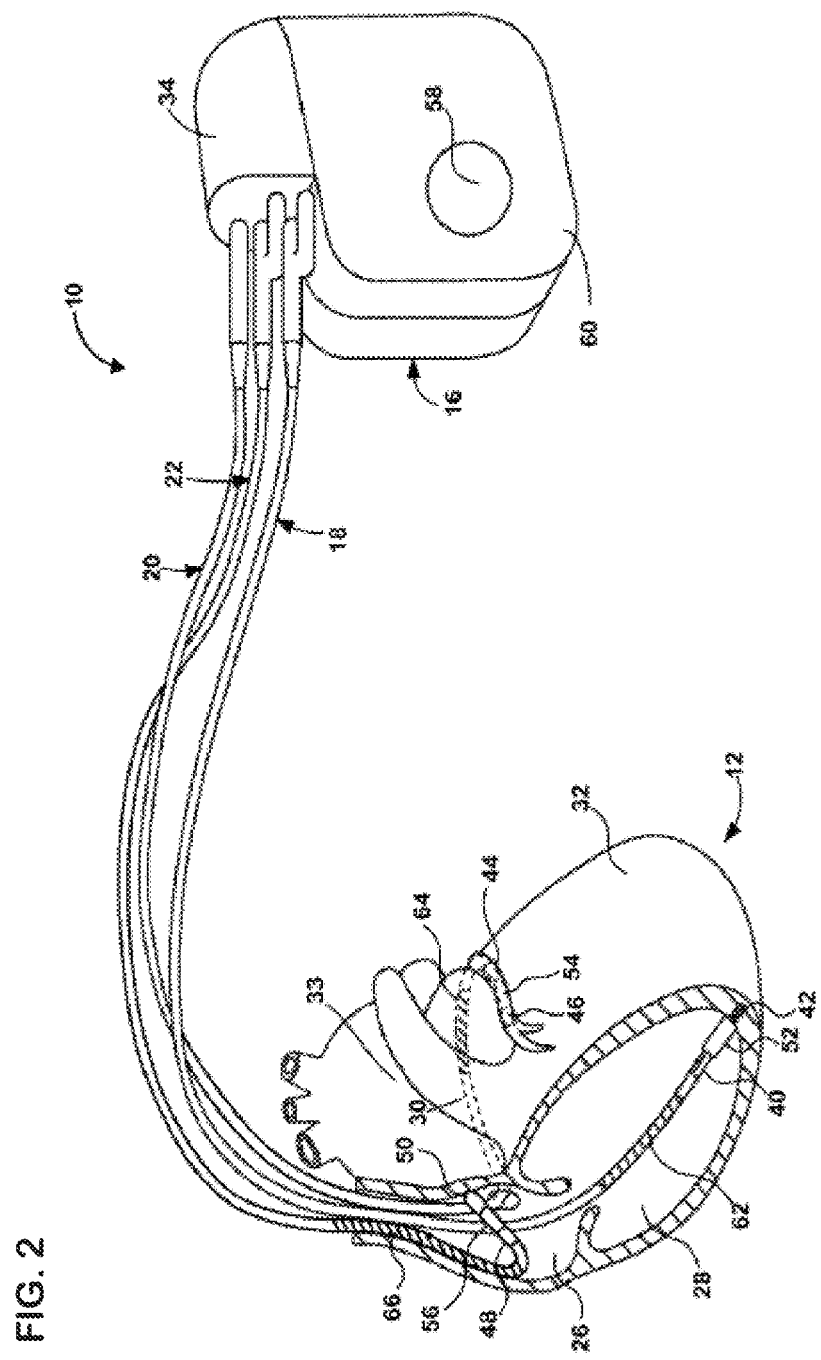
FIG. 2 is a conceptual diagram of the exemplary IMD of FIG. 1 in more detail.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. An example of a configuration sensing and pacing may be seen with respect to U.S. Pat. Application No. 61/580,058 filed Dec. 23, 2011, and assigned to the assignee of the present invention, the disclosure of which is incorporated by reference in its entirety herein as modified by preferably using a LVtip (i.e. electrode 46)—Rvcoil (i.e. electrode 62) for the pacing vector and the sensing vector. It is generally understood by those skilled in the art that other electrodes can also be selected as pacing and sensing vectors. Electrode 44 and 64 refer to the third and fourth LV electrodes in the claims.

As described in further detail with reference to FIGS. 3A-3B, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3A:
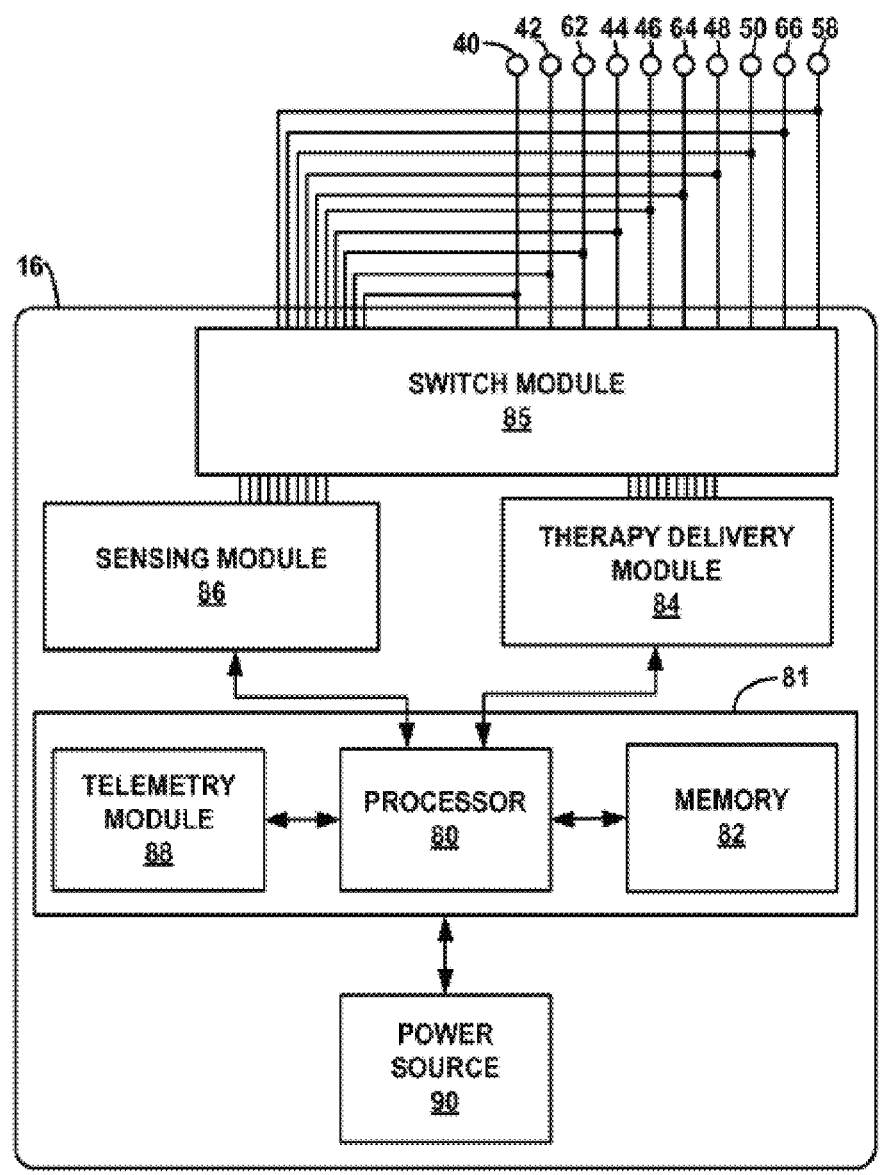
FIG. 3A is a block diagram of an exemplary IMD, e.g., the IMD of FIGS. 1-2.

FIG. 3A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. Memory 82 includes computer instructions related to capture management. An exemplary capture management module such as left ventricular capture management (LVCM) is briefly described in U.S. Pat. No. 7,684,863, which is incorporated by reference. As to the delivery of pacing stimuli, capture management algorithms typically focus on sufficient energy delivery of a pacing stimulus.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to analyze of a plurality of paced events. More specifically, one or more morphological features of each paced event within the ECG/EGM signals may be used to determine whether each paced event has a predetermined level of effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart (e.g., one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness. For example, the processor 80 may be configured to determine, or obtain, one more features of one or more sensed morphological waveforms within one of more electrical vectors of the patient's heart and store the one or more features within the memory 82 for use in determining effectiveness of pacing therapy at a later time.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (e.g., does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

A pacing (e.g., for LV and/or BV pacing) ratio or percentage, which is the number of paced heart beats divided by the total number of heart beats, often expressed as a percentage of the total number of heart beats, may be a useful metric for evaluating the effectiveness of CRT but, in many cases, it may be misleading because a high pacing ratio or percentage may not necessarily mean that CRT is effective if, e.g., ventricular pacing fails to properly alter electrical activation patterns. Automatic beat-to-beat analysis of the evoked response (e.g., paced QRS complexes) in monitored EGM signals may be used to determine whether the paced heartbeat was effectively paced, and hence, to provide more resolution to a pacing ratio. For example, the heartbeats that were paced but determined to not be effectively paced (e.g., depending on the degree of fusion between intrinsic and paced activation, etc.) may be excluded from the pacing ratio thereby providing a more accurate metric of pacing efficacy and/or efficiency, which may referred to as a pacing effectiveness ratio.

A feature-based classification may enable beat-to-beat rhythm classification in a device (e.g., IMD 16) employing cardiac pacing (e.g., left ventricular fusion pacing, biventricular pacing, etc.) and may add value to the device by providing useful diagnostic indices to a physician. The computational price involved in such feature-based beat-to-beat classifications may be minimal and may be implemented within the architecture of devices such as the IMD 16 described herein with reference to FIGS. 1-3B. For example, the exemplary methods described herein may combine algebraic operations and comparisons and/or may require a single normalization per beat compared to multiple intensive mathematical operations and normalizations that are often required for detailed template matching algorithms.

Figure 3B:
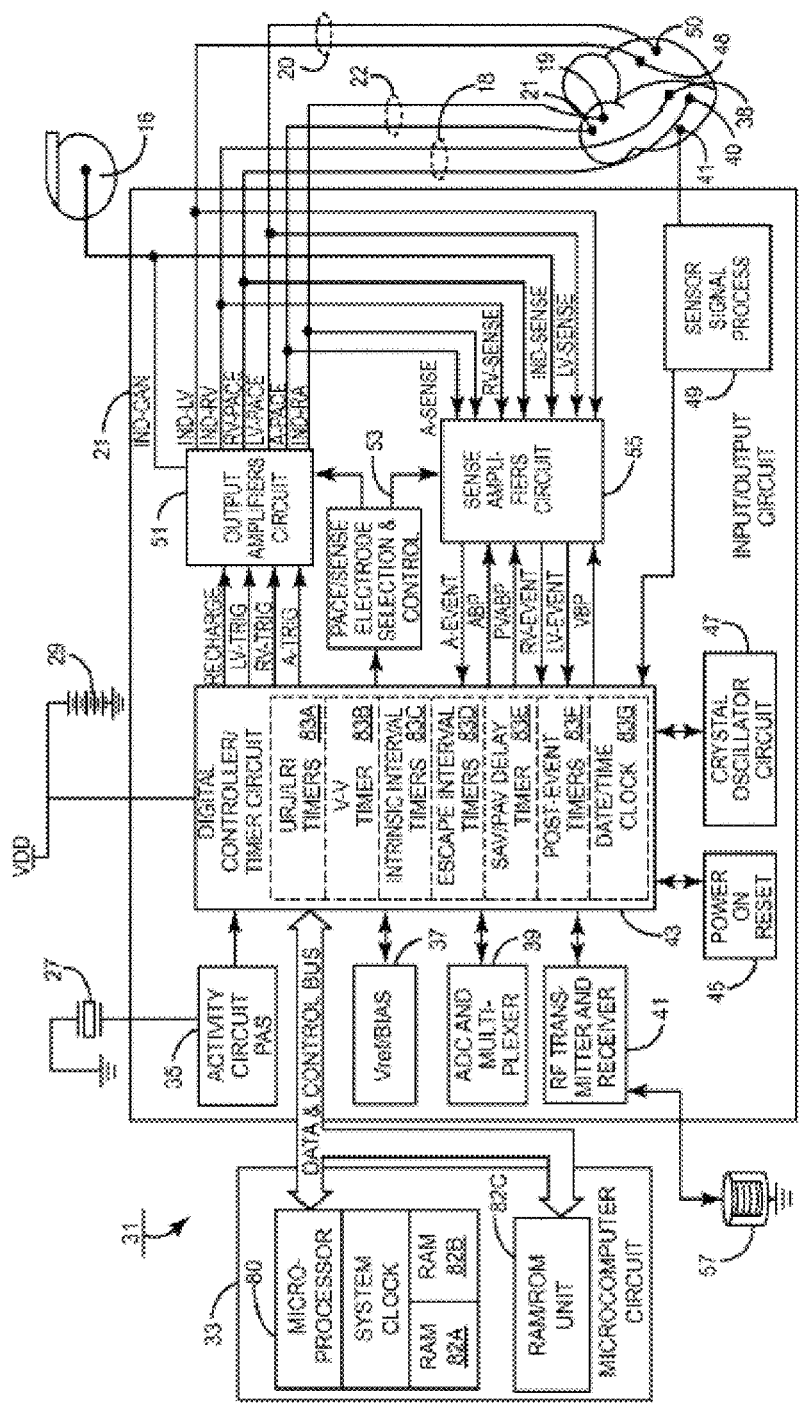
FIG. 3B is yet another block diagram of one embodiment of IMD (e.g. IPG) circuitry and associated leads employed in the system of FIG. 2 for providing three sensing channels and corresponding pacing channels that selectively functions in a ventricular pacing mode providing ventricular capture verification.

FIG. 3B is yet another embodiment of a functional block diagram for IMD 16. FIG. 3B depicts bipolar RA lead 22, bipolar RV lead 18, and bipolar LV CS lead 20 without the LA CS pace/sense electrodes 28 and 30 coupled with an IPG circuit 31 having programmable modes and parameters of a bi-ventricular DDD/R type known in the pacing art. In turn, the sensor signal processing circuit 43 indirectly couples to the timing circuit 83 and via data and control bus to microcomputer circuitry 33. The IPG circuit 31 is illustrated in a functional block diagram divided generally into a microcomputer circuit 33 and a pacing circuit 83. The pacing circuit 83 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 47 provides the basic timing clock for the pacing circuit 320, while battery 29 provides power. Power-on-reset circuit 45 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 320, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 45 and crystal oscillator circuit 47 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 35 in the depicted, exemplary IPG circuit 31. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 35 and provided to digital controller/timer circuit 83. Activity circuit 35 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 374 for timing post-ventricular time periods, and a date/time clock 376.

The AV delay interval timer 83E is loaded with an appropriate delay interval for one ventricular chamber (i.e., either an A-RVp delay or an A-LVp delay as determined using known methods) to time-out starting from a preceding A-PACE or A-EVENT. The interval timer 83E triggers pacing stimulus delivery, and can based on one or more prior cardiac cycles (or from a data set empirically derived for a given patient).

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The exemplary methods and/or devices described herein may track, or monitor, the effectiveness of pacing therapy by analyzing one or more features of a sensed morphological waveform corresponding to a paced event for one or more monitored electrical vectors of the patient's heart. As used herein, a sensed morphological waveform may correspond to a paced event by occurring within a predetermined, or selected, time period, or sensing window, (e.g., 200 milliseconds) after the delivery of pacing stimulus. The sensed morphological waveform may, e.g., result from the delivery of pacing stimulus and/or intrinsic conduction.

Figure 4:
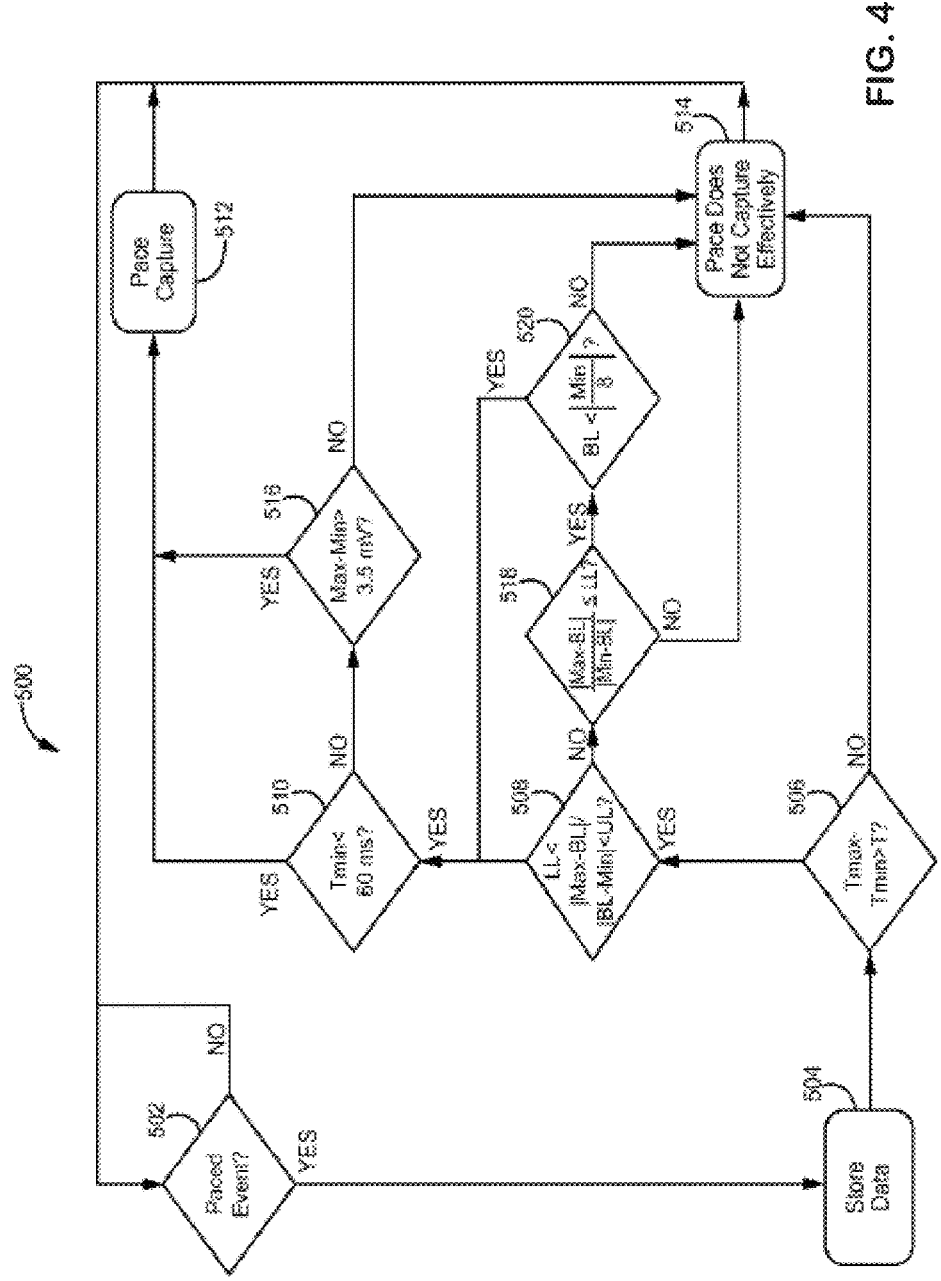
FIG. 4 is a flowchart of an exemplary method for determining whether an electrical stimuli effectively captures a ventricle.

FIG. 4 depicts a diagnostic method 500 for use in determining pacing effectiveness in CRT pacing. In particular, morphological features following delivery of a paced event are compared to absolute levels (i.e., thresholds that are not patient specific). For example, exemplary systems and methods described herein monitor one or more electrical vectors of a patient's heart during pacing therapy, analyzing whether each paced event has a predetermined level of effectiveness. In one or more embodiments, morphological features are evaluated of a LV electrode-RV coil vector during LV only pacing or biventricular (BV) pacing in CRT. Exemplary LV electrode-RV coil vector can include electrode pairings such as a LV tip (e.g. electrode 46) to RV coil (e.g. electrode 62), or LV ring (e.g. electrode 54) to RV coil (e.g. electrode 62). It is advantageous to select a monitoring vector that includes the LV pacing cathode and another electrode such as a RV coil or the IMD 16 case or housing. For example, if LV pacing is occurring at the LV tip, then it is preferable to employ a monitoring vector of Lvtip-Rvcoil or Lvtip-device case.

Figure 5:
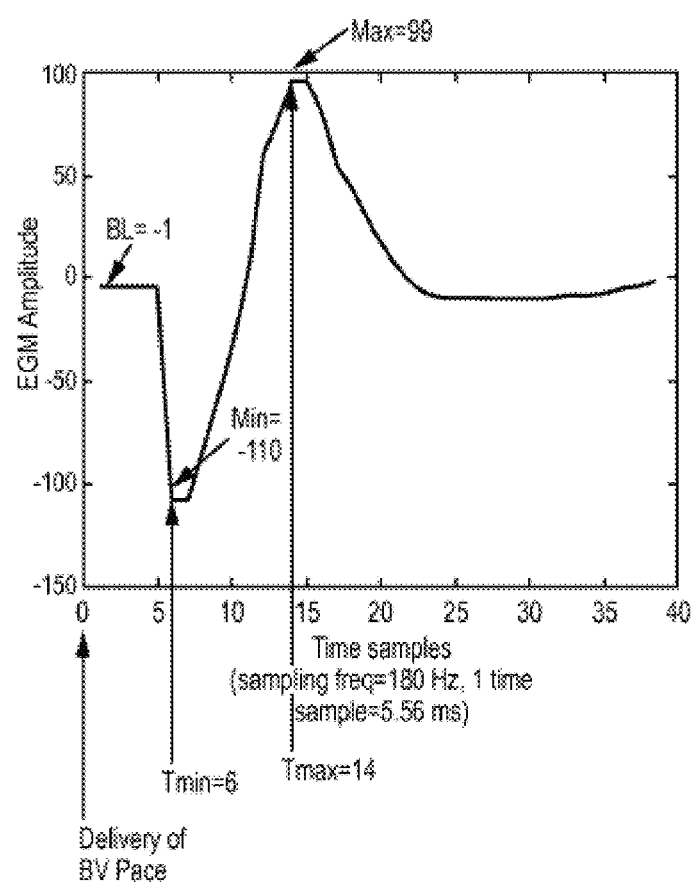
FIG. 5 graphically depicts data that supports an effective capture test depicted in flowchart of FIG. 4.

At block 502, a determination is made as to whether a current or latest ventricular event is a paced event. If the device did not deliver a paced event, the NO path is followed, returning to block 502 to continue checking for the next paced event. If a paced event has occurred, the YES path continues to optional block 504 so that the electrogram data from the monitored vector can be stored into memory. Block 504 is optional since data storage can automatically occur independently of the computer instructions set forth in method 500. Exemplary EGM data resulting from a paced event is depicted in FIG. 5. As shown, electrical stimuli (e.g. a biventricular pacing pulse) was delivered through a medical electrical lead to cardiac tissue at time=0 while the data is sampled at an exemplary sampling frequency of 180 Hz (5.56 ms per sample). Baseline data value (BL), used as a reference value, is sensed immediately before a pacing stimulus is delivered. In the example of FIG. 5, the device holds the baseline data value during a period of blanking that immediately precedes and follows the delivery of a pacing stimulus, so the BL can also be sensed during the holding period (i.e., immediately after a pacing stimulus is delivered). For example, the BL EGM amplitude is −1 and the minimum EGM amplitude is −110 where the units are equal to the least significant bit (LSB) voltage of the analog-to-digital converter (ADC). By way of illustration, if the full scale voltage range of the ADC is 8 millivolts (mV) and the ADC has a 8 bit resolution then the LSB voltage is 8*1000/(2.sup.8-1)=31.3 microvolts (.mu.V). The timing of the minimum amplitude occurs at 6 time-samples (i.e., 33.4 milliseconds (ms)) from the time the pacing stimulus is initially delivered to cardiac tissue. After the delivery of the pacing stimulus, the maximum EGM amplitude is 99 and the timing of the maximum amplitude is 14 time-samples (i.e. 78.4 ms).

Morphological features are parsed from an EGM and are used to determine whether pacing is effectively capturing a ventricle. Exemplary morphological features include maximum value (Max), timing of maximum value (Tmax), minimum value (Min), timing of minimum value (Tmin), baseline value (BL) of the EGM amplitude at the time at which pace was delivered. The morphological features are evaluated within a time-window of pre-specified width (i.e. 200 ms) starting at the time of delivery of pacing.

To determine whether a pacing stimulus effectively captures a ventricle, sensed data is evaluated according to one or more of the mathematical relationships embodied at blocks 506, 508, 510, 516, 518, and 520. At block 506, a determination is made as to whether a first condition relative to effective capture is met. The first condition, presented below, subtracts Tmin from Tmax and then determines whether the result is greater than a predetermined threshold (T) such as 30 ms. The equation for the first condition is as follows:

$$Tmax-Tmin>30\ ms$$

If Tmax−Tmin is not greater than 30 ms, then the NO path continues to block 514 in which the pacing stimulus is declared to ineffectively capture a ventricle. In contrast, if Tmax−Tmin>30 ms, the YES path continues to block 508. The data presented in FIG. 5 provides an example of this condition being satisfied since Tmax−Tmin is equal to 78.4-33.4 ms which equals 45 ms. At block 508, a determination is made as to whether a second condition is met. The equation for the second condition is as follows:

$$LL<|Max-BL|/|BL-Min|<UL.$$

The lower limit (LL) and upper limit (UL) are associated with upper and lower ratio limits, respectively, of a morphological feature. Exemplary LL can be 0.2 with a range of 0.1 to 0.33 and exemplary UL can be 5.0 with a range of 3.0 to 10.0. Preferably, LL is set at 0.125 and the UL is set at 8.0.

The maximum value (Max) and the minimum value (Min) are associated with a particular EGM morphological feature such as amplitude. The ratio, |Max−BL|/|BL−Min|, includes the absolute value of Max−BL which is divided by the absolute value of BL−Min. If the second condition at block 508 is not satisfied, then the NO path continues to block 518 in which a determination is made as to whether (|Max−BL|/|Min−BL|).ltoreq.LL. If (|Max−BL|/|Min−BL|).ltoreq.LL is not met, then the NO path continues to block 514 and the ventricular pace stimuli is declared not to evoke effective capture of the ventricle. In contrast, the YES path from block 518 continues to block 520 in which a determination is made as to whether BL<|Min/8|. If BL is not less than |Min/8|, the NO path from block 520 continues to block 514 in which the electrical stimuli is declared to ineffectively capture the ventricle. If BL is less than |Min/8|, then the YES path continues to optional block 510.

The YES path from block 508 also continues to block 510 which determines whether Tmin is less than a preselected value such as 60 ms. The preselected value can be any value between 40 ms-80 ms. If Tmin is not less than 60 ms, then the NO path continues to optional block 516 in which another determination is made as to whether Max-Min is greater than 3.5 mV. If Max-Min is greater than 3.5 mV, effective capture exists and the YES path continues to block 512 in which the ventricular stimulus is declared to capture the ventricle. The NO path from block 516 continues to block 514 in which a determination is made that ventricular stimulus is determined not to effectively capture a ventricle.

Returning to block 510, if Tmin is less than 60 ms, then the YES path continues to block 512 in which effective capture is declared. Every time effective capture is declared at block 512, an effective capture counter is incremented by 1. The effective capture counter is maintained and updated continuously during effective capture monitoring. Effective capture monitoring determines whether pacing stimulus is effective or ineffective. Effective capture monitoring tracks responses from cardiac tissue during pacing therapy.

Effective capture monitoring may be performed continuously or, more preferably, performed periodically (e.g. 100 beats/hour (hr), daily etc.) in order to conserve battery life. Preferably, effective capture monitoring is performed 100 beats per hour and consists of normal pace timings (not the ideal timing conditions of ECT). The effective capture monitoring (i.e. 100 beats per hour) is reported to the user as a % of effective capture beats. The user can apply any choice of threshold for concern (e.g. 90%, etc.).

After a period of monitoring, a metric of effective capture can be computed by dividing the effective capture counter by the total number of paced beats. The method then returns to monitoring for the next paced event at block 502.

To determine if effective LV capture can occur under ideal conditions, an effective capture test (ECT) is performed periodically (e.g. daily, etc.), upon the direction of a user (e.g. while the patient sleeps such as at night time), or in response to consistent observation of ineffective capture. Generally, ideal conditions relate to delivering a pacing stimulus at an adequate amplitude and time.

The result of the ECT can be used to explain reasons for the observation of ineffective capture throughout the day. For example, if a left ventricular lead is dislodged, if scar tissue develops at the location of LV pacing, or if BV pacing includes substantial pre-excitation of the RV, it may not be possible to obtain effective LV capture even under ideal conditions.

The ECT test can be performed for LV only pacing or BV pacing. The manner in which the ECT is performed depends upon whether the patient is experiencing atrial fibrillation (AF). AF generally results in switching of pacing behavior to a pacing mode that does not track atrial activation (e.g., DDI, DDIR, VVI, or VVIR pacing modes). When not in AF, the device generally is operating in a pacing mode that tracks atrial activation, such that SAV and PAV are relevant pacing timing parameters. For example, if the patient is not in AF, LV-only pacing employs a very short PAV (e.g. 10 ms) or SAV (e.g. 10 ms). Alternatively, if the patient is experiencing AF, LV-only pacing employs an overdrive rate. Test beats (e.g. 5 test beats, etc.) are delivered to a ventricle to determine whether the ventricle was effectively captured in accordance with the criteria presented in FIG. 4 and the accompanying text. If, for example, 75% of the tested beats such as 4 of 5 beats are effectively captured, the ECT is passed for that day. Passing the ECT for that day means that effective capture is at least possible under ideal conditions.

The BV test follows the LV test. For the BV test, a very short PAV or SAV is used along with the currently programmed VV delay if the patient is not in AF, and an overdrive rate is employed if the patient is in AF. Again, 5 test beats are delivered with BV pacing, and 4 of 5 must pass effective LV capture. LV paced beat or BV paced beat is deemed to provide effective capture if the morphological features satisfy the effective capture test (ECT). The ECT can comprise one, two or three of the following relationships:

$$T\text{max} - T\text{min} > 30 \text{ ms} \quad (1)$$

$$0.2 < |\text{Max} - \text{BL}|/|\text{BL} - \text{Min}| < 5 \text{ or } (|\text{Max} - \text{BL}|/|\text{Min} - \text{BL}|.\text{ltoreq.LL and BL} < |\text{Min}/8|) \text{ and} \quad (2)$$

$$T\text{min} < 60 \text{ ms or Max} - \text{Min} > 3.5 \text{ mV} \quad (3)$$

All timing parameters are measured from the time at which the pace is delivered.

Figure 6:
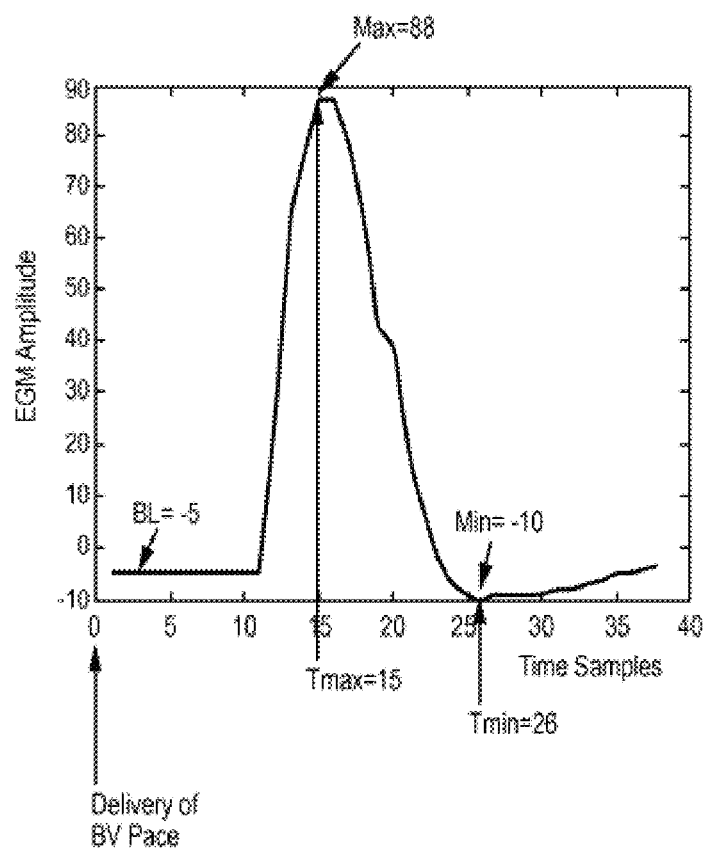
FIG. 6 graphically depicts data, used in the flowchart of FIG. 4, in which effective capture has not occurred.
Figure 7:
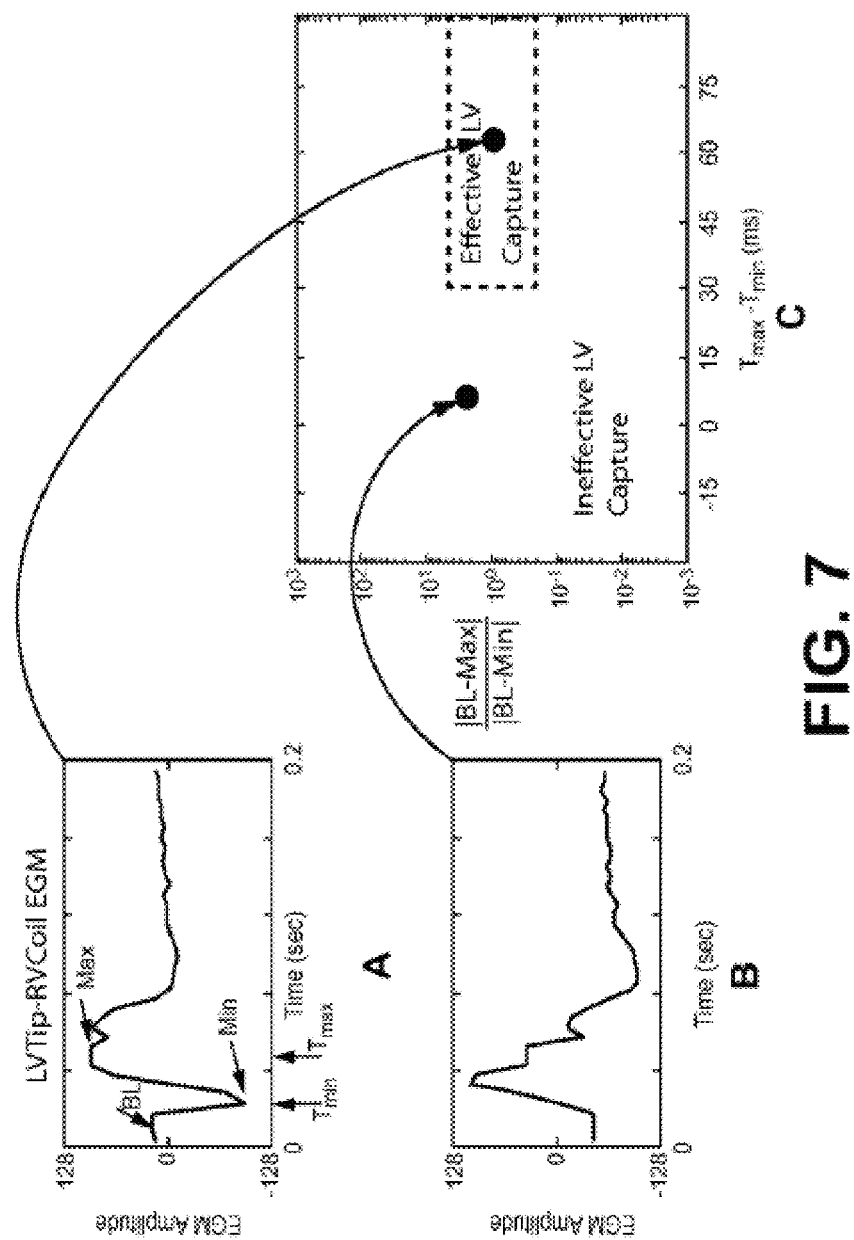
FIGS. 7A-7C graphically depicts data that supports an effective capture test depicted in flowchart of FIG. 4.

Table 1 summarizes exemplary method 500 diagnostic data. The two different examples of diagnostic data, shown in FIGS. 5 and 6, depict R waves from the QRS complex of the cardiac cycle. The R wave, a depolarization of the ventricles, generally has an amplitude greater than any other wave of the cardiac cycle and is characterized by a rapid deviation from and return toward baseline.

FIG. 5 shows a negative deflection preceding a positive deflection while FIG. 6 depicts a positive deflection preceding a negative deflection of the signal. A negative deflection occurs when a curve falls below the base line. A negative deflection indicates that a recorded far field wave has traveled away from one of the electrodes on a lead. In contrast, a positive deflection occurs when a curve rises above the base line as depicted in FIG. 6. The positive deflection means the recorded far field wave has traveled toward the electrode.

Turning now to the application of the ECT criteria, the pacing data presented in FIG. 5 delivered effective pacing to capture the ventricle since blocks 506, 508 and 510 of FIG. 4 were successfully passed. Pacing data presented in FIG. 6 ineffectively captured the ventricle since Tmax−Tmin is not greater than 30 ms as to block 506. Table 1 lists the ECT criteria along with each result for the pacing data presented in FIGS. 5 and 6.

TABLE 1

Summary of two different pacing effectiveness examples.

| Parameter or condition | Example 1-FIG. 5 | Example 2-FIG. 6 |
| --- | --- | --- |
| Tmax | 78.4 ms | 83.4 ms |
| Tmin | 33.4 ms | 144.6 ms |
| BL | −1 | −5 |
| Min | −110 | −10 |
| Max | 99 | 88 |
| Tmax − Tmin > 30 | 78.4 − 33.4 > 30 | 83.4-144.6 is less than zero; therefore, pacing stimulus does not effectively capture |
| 0.2 < \|Max − BL\|/ \|BL − Min\| < 5 | 0.2 < \|.99\| < 5 | Does not test for this condition |
| Tmin < 60 ms | 33.4 ms < 60 ms | Does not test for this condition |
| Effectively pacing? | Yes | No |

The conditions for classifying a paced beat as effective or ineffective capture can be conveniently displayed as a two-dimensional scatter plot. FIGS. 7A-7C support conditions found in the flow chart of FIG. 4. FIGS. 7A-7B depict a LVtip-RV coil EGM. The EGM amplitude, along the Y-axis, extends from −128 to 128 while the X-axis extends from 0 to 0.2 seconds. Data such as BL, Min, Max, Tmin, Tmax are shown for each stimuli and are compared to the criteria for effective capture. The data is then mapped onto the scatter plot of FIG. 7C. As shown, effective capture exists within the boxed area from the stimuli delivered from FIG. 7A while ineffective capture exists outside of the boxed area as evoked from the electrical stimuli delivered from FIG. 7B. Note that the third criterion for effective capture (Tmin<60 ms or Max−Min>3.5 mV) is not included in this graphical depiction and is not required for effective capture determination in one or more other embodiments.

Figure 8:
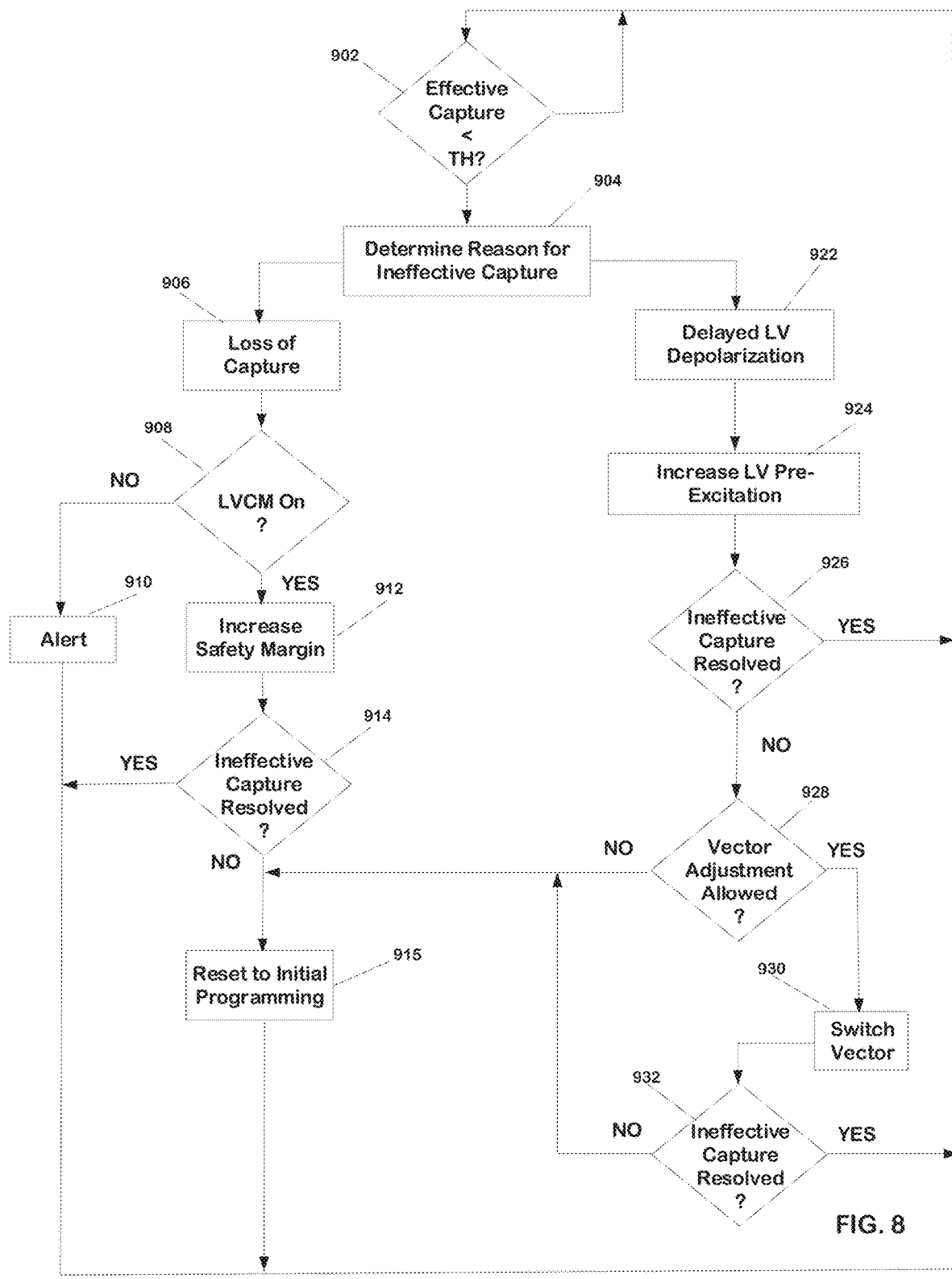
FIG. 8 is a flowchart of another exemplary method for automatically adjusting settings on an implantable medical device to more effectively capture a ventricle.

FIG. 8 is a flowchart of an exemplary method of delivering a cardiac resynchronization therapy in an implantable medical device according to an example of the present disclosure. As illustrated in FIG. 8, during delivery of a cardiac resynchronization therapy according to an example of the present disclosure, the processor 80 determines whether effective capture resulting from the delivered CRT pacing is less than a predetermined threshold for the latest period of time (e.g. 5 days), Block 902. As described above, an exemplary predetermined threshold may be set at 80% and could range from, for example, 98% to 50%. Additionally, while the latest period of time could be set at 5 days, it should be appreciated that the latest period of time could range from 1 hour to 14 days. In another example, the predetermined threshold may be relative to the percentage of CRT pacing delivered. For example, if 90% of CRT pacing is delivered, but only 80% is effective, this "delta" of 10 percent may be compared to a percentage delta threshold.

The reason for ineffective capture is accessed by the processor 80 from memory 82, Block 904. An example method for determining loss of capture or latency as the reason for ineffective capture are described, for example, in U.S. Pat. No. 9,320,905 to Ghosh et al., incorporated by reference in its entirety. In another example according to the present disclosure, in order to determine loss of capture as being the reason for ineffective capture, the processor 80 may determine whether a difference between the percentage of V-paced (VP) beats and the percentage of effective CRT during a predetermined time period is greater than or equal to a difference threshold, such as 5 percent during the last 24 hours, for example.

If the difference between the percentage of V-paced (VP) beats and the percentage of effective CRT is greater than or equal to the difference threshold, the processor 80 may also determine whether at least one of two additional requirements are met. For example, the processor 80 may further determine whether either, (1) a predetermined time period has expired since implant, such as 14 days for example, LCVM capture thresholds have been unavailable for a predetermined number of days, such 9 out of the last 14 days, for example, and LVCM capture thresholds are unavailable for the most recent day, or (2) a difference between the minimum and maximum LVCM capture thresholds over a predetermined number of days, such as 14 days for example, for the current LV path and LV pulse width is greater than or equal to a min/max difference threshold, such as the current amplitude safety margin minus 25 volts, for example.

In this way, according to one example, the reason for ineffective capture, Block 904, may be determined to be loss of capture, Block 906, if the processor 80 determines that the difference between the percentage of V-paced (VP) beats and the percentage of effective CRT is greater than or equal to the difference threshold, and at least one of additional requirement (1) and additional requirement (2) is satisfied.

When the reason for ineffective capture is determined to be loss of capture, Block 906, the processor 80 determines whether the LVCM feature has been turned on or enabled, and the LV safety margin has been programmed to "automatic", Block 908. If LVCM is determined to be not enabled, No in Block 908, the processor 80 may generate an alert or an observation of the determined ineffective capture, Block 910, and the process is repeated with determining whether effective capture is less than the predetermined threshold after expiration of the next period of time, Block 902.

If LVCM is determined to be enabled, Yes in Block 908, the processor 80 may increase the baseline safety margin of amplitude over the required amplitude for ventricular capture by a predetermined level, such as 0.5 volts for example, Block 912. In additional examples, the safety margin may be in pulse width, or a combination of amplitude and pulse width. In another example, the processor may execute a capture management algorithm to determine an adjusted capture threshold if LVCM is determined to be enabled, Yes in Block 908. The processor 80 then determines whether the ineffective capture has been resolved when pacing is delivered using the adjusted safety margin or the adjusted capture threshold, Block 914. For example, in order to confirm that the adjustment of the safety margin was effective in resolving the ineffective capture, the processor 80 may monitor the pacing therapy for a predetermined period of time, such as 24 hours for example, and determine whether there has been a change in effective CRT during that 24 hour period. As another example, in order to determine a change in effective CRT, after waiting for a predetermined number of beats, such as two beats, for example, to enable transition of the device to the adjusted output, a predetermined number of subsequent beats are subsequently analyzed for effective CRT during the 24 hour period, such as 5 beats for example.

In one example, if less than 4 of the 5 subsequent beats are determined to result in effective capture, a change is not determined to have occurred and therefore ineffective capture is not resolved, No in Block 914. The initial programming is reset, Block 915, including resetting of the LV safety margin or capture threshold from the adjusted value to the initial value, along with resetting the VV-delay or LV pacing vector as appropriate, and the process is repeated with determining whether effective capture is less than the predetermined threshold after expiration of the next period of time, Block 902. On the other hand, if 4 or more of the 5 beats are determined to result in effective capture, a change is determined to have occurred and therefore ineffective capture is resolved, Yes in Block 914. As a result, the pacing therapy is continued to be delivered with the adjusted LV safety margin or capture threshold, and the process is repeated with determining whether effective capture is less than the predetermined threshold after expiration of the next period of time, Block 902. In one example, the safety margin or capture threshold may be subsequently reset when LVCM or the LV safety margin is reprogrammed.

In this way, if the reason for ineffective capture is determined to be a loss of capture, the processor 80 may adjust the safety margin or capture threshold from a baseline setting, and if the ineffective capture is not resolved using the adjusted safety margin or capture threshold, return to the baseline safety margin. In addition, if LVCM is determined to be not enabled or turned off, the processor 80 merely generates an alert or an observation without making any adjustments.

According to one example, in order to determine delayed depolarization as being the reason for ineffective capture, Block 922, i.e., resulting from the lead being positioned within scar tissue or within latent or inactive tissue, the processor 80 may determine whether a predetermined number of delayed depolarization requirements are satisfied. For example, the delayed depolarization requirements may include (1) that the CRT for the device is programmed to an adaptive biventricular pacing therapy or an adaptive biventricular and left ventricular pacing therapy, and the CRT for the device includes having control over the VV delay. In addition, the requirements may include (2) that CRT pacing is effective for at 4 of 5 LV-only paced cycles and Tmin>100 ms (>13 samples) for at least 4 of the 5 LV-only paced cycle, and (3) that a difference between the percentage of ventricular pacing and percentage of effective CRT during a predetermined time period is greater than or equal to a threshold, such as 5 percent over a 24 hour time period, for example.

In this way, according to one example, the reason for ineffective capture, Block 904, is determined to be delayed LV depolarization, Block 922, if the processor 80 determines that the delayed depolarization requirements (1)-(3) are satisfied, and as a result, a latency remediation flag is set and the processor 80 increases the LV pre-excitation, Block 924, from a baseline value to an adjusted value. For example, the processor 80 may cease automatic control of VV-delay (e.g., from an algorithm that routinely updates the VV delay) and cause the VV-delay to be increased by a predetermined value to a maximum value, such an increasing the VV-delay by 20 ms up to a maximum of 60 ms, for example. In another example, an offset can be applied to the VV-delay determined by an automated algorithm. For example, if a CRT algorithm chooses a VV delay of 20, this new feature will automatically increment the VV delay to 40 ms.

After initially increasing the VV-delay by 20 ms, a determination is made as to whether the ineffective capture is resolved as a result of using the increased LV-pre-excitation, Block 926. For example, in order to confirm that the adjustment of the LV pre-excitation was effective in resolving the ineffective capture, the processor 80 may monitor the pacing therapy for a predetermined period of time, such as 24 hours for example, and determine whether there has been a change in effective CRT during the 24 hour time period. As another example, the processor 80 may analyzed a predetermined number of subsequent delivered paced beats, such as five delivered paced beats for example, and determine whether the beats result in effective capture.

In one example, if four of the five subsequent delivered beats are determined to result in effective capture, ineffective capture is determined to be resolved, Yes in Block 926, and the increased LV pre-excitation is confirmed and the process is repeated, Block 902, with the CRT pacing being delivered at the adjusted VV-delay for a predetermined time period, such as 24 hours for example. If less than four of the five subsequent delivered beats are determined to result in effective capture and the current VV-delay is less than 60 ms, the VV-delay is again increased by 20 ms, and the next five paced beats are analyzed for effective capture, and the process is repeated. On the other hand, if less than four of the five subsequent delivered beats are determined to result in effective capture and the current VV-delay is not less than 60 ms, the ineffective capture is determined not to be resolved, No in Block 926, the control of the VV-delay is restored by the CRT algorithm, the latency remediation flag is removed and latency remediation is delayed for a period of time, such as 24 hours for example.

In this way, if a change in effective CRT is determined to occur and therefore ineffective capture is determined to be resolved by the adjustment of the LV pre-excitation, Yes in Block 926, the process is repeated for CRT delivered having the adjusted LV pre-excitation, to determine whether effective capture is less than the predetermined threshold after expiration of the next period of time, Block 902.

On the other hand, if a change in effective CRT is not determined to occur and therefore ineffective capture is not determined to be resolved by the adjustment of the LV excitation, No in Block 926, the processor 80 returns the adjusted LV pre-excitation to the baseline LV pre-excitation and determines whether current device settings indicate that LV pacing vector adjustment is allowed, Block 928. If the current device settings indicate that vector adjustment is not allowed, No in Block 928, the initial programming is reset, Block 915, including resetting of the LV safety margin from the adjusted value to the initial value, along with resetting the VV-delay or LV pacing vector as appropriate, and the process is repeated with determining whether effective capture is less than the predetermined threshold after expiration of the next period of time, Block 902.

If the current device settings indicate that vector adjustment is allowed, Yes in Block 928, the processor 80 causes the device to switch the sensing vector from the baseline sensing vector formed between electrodes 40, 42, 44, 46, 48, 50, 58 to another sensing vector formed between electrodes 40, 42, 44, 46, 48, 50, 58, Block 930, and determines whether the ineffective capture has been resolved when pacing is delivered using the adjusted pacing vector, Block 932. For example, in order to confirm that the adjustment of the pacing vector was effective in resolving the ineffective capture, the processor 80 may monitor the pacing therapy and determine whether there has been a change in effective CRT, as described above. If a change in effective CRT is determined to occur and therefore ineffective capture is determined to be resolved, Yes in Block 932, the process is repeated with determining whether effective capture is less than the predetermined threshold after expiration of the next period of time, Block 902.

On the other hand, if a change in effective CRT is not determined to occur and therefore ineffective capture is not determined to be resolved, No in Block 932, the processor 80 adjusts the pacing vector back to the baseline pacing vector and the initial programming is reset, Block 915, and the process is repeated with determining whether effective capture is less than the predetermined threshold after expiration of the next period of time, Block 902.

In this way, if the reason for ineffective capture is determined to be delayed LV depolarization, the processor 80 may adjust the LV pre-excitation from a baseline LV pre-excitation setting, and if the ineffective capture is not resolved as a result of the adjusted LV pre-excitation, return the LV pre-excitation back to the baseline setting. The processor 80 then determines whether current device settings indicate that vector adjustment is allowed, and if it is determined that vector adjustment have been indicated as being allowed, the processor 80 may switch the current pacing vector from the baseline pacing vector to an adjusted pacing vector, and subsequently determined whether the ineffective capture is resolved as a result of the adjustment of the pacing vector.

Figure 9:
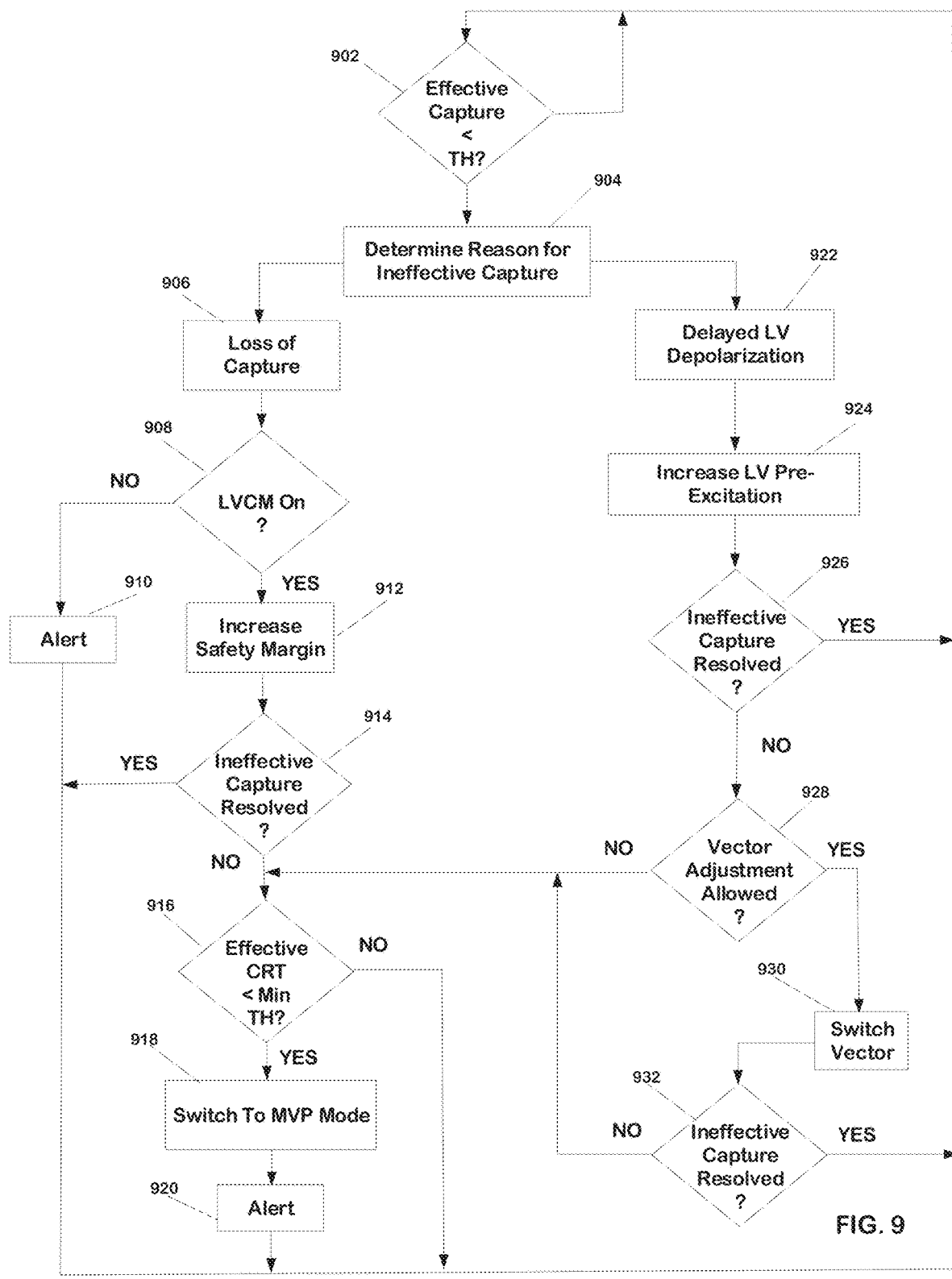
FIG. 9 is a flowchart of an exemplary method of delivering a cardiac resynchronization therapy in an implantable medical device.

FIG. 9 is a flowchart of an exemplary method of delivering a cardiac resynchronization therapy in an implantable medical device according to an example of the present disclosure. The method of FIG. 9 includes all of the features of the method of claim 8, which are not repeated here for brevity sake. However, the example of FIG. 9 differs in that the example of FIG. 9 includes additional features for determining whether ineffective capture has been resolved when loss of capture is the determined reason for ineffective capture. In one example, such additional features may be indicative of an elevated concern over LV loss of capture representative of an increased level of failure in LV capture, which results in detrimental RV-only pacing.

In particular, as illustrated in FIG. 9, if ineffective capture is not resolved as a result of the adjustment to the safety margin or capture threshold, No in Block 914, or if vector adjustment is not allowed, No in Block 928, or if ineffective capture is not resolved, No in Block 932, the processor 80 may determine whether the determined effective CRT is less than a minimum effective CRT threshold, Block 916. If the current determined effective CRT is not less than the minimum effective CRT threshold, No in Block 916, the process is repeated with determining whether effective capture is less than the predetermined threshold after expiration of the next period of time, Block 902. While the use of a minimum delta between delivered CRT and effective CRT is described, in another example, the determination may be associated with there being a large delta between delivered CRT and effective CRT.

In one example, the processor 80 may make the determination of whether the determined effective CRT is less than a minimum effective CRT threshold, Block 916, based on multiple features, such as (1) whether effective CRT is determined to be less than a predetermined percentage over a given time period, such as 10% effective CRT during the most recent day, for example, (2) the LV pacing vector has not been adjusted in a predetermined period of time, such as 48 hours, for example, (3) effective CRT has been greater than a predetermined threshold over a given number of days, such as greater than 50% effective CRT for one or more days of the most recent 3 days, for example, and (4) effective CRT episodes have been determined over a given time period, such as 5 days for example.

If all of additional features (1)-(4) are not satisfied, the current determined effective CRT is determined not to be less than the minimum effective CRT threshold, No in Block 916, and the process is repeated with determining whether effective capture is less than the predetermined threshold after expiration of the next period of time, Block 902. On the other hand, if all of additional features (1)-(4) are satisfied, the current determined effective CRT is determined to be less than the minimum effective CRT threshold, Yes in Block 916, the processor 80 may switch the pacing mode to a minimum ventricular pacing (MVP) mode, Block 918, generate an alert or an observation of the determined ineffective capture, Block 920, and the process is repeated with determining whether effective capture is less than the predetermined threshold after expiration of the next period of time, Block 902.

MVP operates to promote intrinsic conduction by reducing unnecessary right ventricular pacing. During an MVP mode protocol, atrial-only pacing is delivered unless intrinsic ventricular events are not sensed. When a ventricular event is not sensed between two consecutive atrial events, a ventricular backup pacing pulse may be delivered after the second atrial event to avoid another cardiac cycle of asystole. When a specified number of atrial-only pacing cycles occur without sensing a ventricular event, the pacing device switches to a dual chamber pacing mode and delivers atrial and ventricular pacing pulses coordinated at a programmed atrial-ventricular (AV) delay.

In this way, if the reason for ineffective capture is determined to be a loss of capture, the processor 80 may adjust the safety margin from a baseline setting, and if the ineffective capture is not resolved using the adjusted safety margin, return to the baseline safety margin and determine whether there is very low percentage of effective CRT at baseline settings. If it is determined that there is very low percentage of effective CRT at baseline settings, the processor 80 may switch the current LV pacing to an MVP mode and generate an alert. If LVCM is determined to be not enabled or turned off, the processor 80 merely generates an alert or an observation without making any adjustments.

If the reason for ineffective capture is determined to be delayed LV depolarization, the processor 80 may adjust the LV pre-excitation from a baseline LV pre-excitation setting, and if the ineffective capture is not resolved as a result of the adjusted LV pre-excitation, return the LV pre-excitation back to the baseline setting. The processor 80 then determines whether current device settings indicate that vector adjustment is allowed, and if it is determined that vector adjustment has been indicated as being allowed, the processor 80 may switch the current pacing vector from the baseline pacing vector to an adjusted pacing vector, and subsequently determined whether the ineffective capture is resolved as a result of the adjustment of the pacing vector. On the other hand, if vector adjustment has not been indicated as being allowed, the processor 80 may determine whether there is very low percentage of effective CRT at baseline settings. If it is determined that there is very low percentage of effective CRT at baseline settings, the processor 80 may switch the current LV pacing to an MVP mode and generate an alert. If LVCM is determined to be not enabled or turned off, the processor 80 merely generates an alert or an observation without making any adjustments.

The techniques described in this disclosure, including those attributed to the IMD 16, the programmer 24, the processor 80 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware components, software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description

ILLUSTRATED EMBODIMENT

Embodiment 1

An implantable medical device system for delivering cardiac resynchronization therapy (CRT) pacing, comprising: an implantable medical device housing; at least one lead having a lead body and capable of being electrically coupled to the housing; a plurality of electrodes positioned along one or both of the device housing and the lead body of the at least one lead to sense a cardiac signal of the patient and to deliver the CRT pacing; and a processor positioned within the housing and configured to determine capture associated with the delivered CRT pacing is ineffective in response to the delivered CRT pacing, determine a reason for capture being ineffective, and adjust one of a safety margin and a capture threshold in response to the determined reason for capture being ineffective being loss of capture and adjusting a left ventricle (LV) pre-excitation in response to the determined reason for capture being ineffective being delayed LV depolarization.

Embodiment 2

The system of embodiment 1, wherein the processor is configured to determine whether a left ventricular capture management (LVCM) feature is enabled, generate an alert in response to the LVCM not being enabled, and adjust the one of the safety margin and the capture threshold in response to the LVCM feature being enabled.

Embodiment 3

The system of any of embodiments 1 and 2, wherein the processor is configured to determine whether a change in effective CRT occurs in response to the CRT pacing being delivered subsequent to performing one of adjusting of the one of the safety margin and the capture threshold and adjusting of the LV pre-excitation, determine ineffective capture as being resolved in response to the change in effective CRT being determined to occur, and determine ineffective capture as not being resolved in response to the change in effective CRT not being determined to occur.

Embodiment 4

The system of any of embodiments 1-3, wherein the processor is configured to adjust the LV pre-excitation from a baseline LV pre-excitation to an adjusted LV pre-excitation, determine whether ineffective capture is resolved in response to the CRT pacing having the adjusted LV pre-excitation being delivered, adjust the LV pre-excitation from the adjusted LV pre-excitation to the baseline LV pre-excitation in response to determining ineffective capture as not being resolved, determine whether a vector adjustment feature associated with adjusting a vector for delivering the CRT pacing has been enabled in response to ineffective capture being determined as not being resolved, and adjust the vector for delivering the CRT pacing in response to the vector adjustment feature being determined to be enabled.

Embodiment 5, the system of embodiment 4, wherein the processor is configured to determine whether ineffective CRT is less than a minimum effective CRT threshold in response to the vector adjustment feature being determined to be not enabled, and switch to a minimum ventricular pacing mode and generating at least one of an alert and an observation of the determination of ineffective capture in response to effective CRT being less than the minimum effective CRT threshold.

Embodiment 6

The system of embodiment 4, wherein the processor is configured to determine whether ineffective capture is resolved in response to the CRT pacing having the adjusted vector being delivered, determine whether effective CRT is less than a minimum effective CRT threshold in response to ineffective capture not being resolved in response to the CRT pacing having the adjusted vector being delivered, and switch to a minimum ventricular pacing mode and generating at least one of an alert and an observation of the determination of ineffective capture in response to effective CRT being less than the minimum effective CRT threshold.

Embodiment 7

The system of any of embodiments 1-6, wherein the processor is configured to adjust the safety margin from a baseline safety margin to an adjusted safety margin, determine whether ineffective capture is resolved in response to the CRT pacing having the adjusted safety margin being delivered, adjust the safety margin from the adjusted safety margin to the baseline safety margin in response to determining ineffective capture as not being resolved, determine whether effective CRT is less than a minimum effective CRT threshold in response to ineffective capture not being resolved in response to the CRT pacing having the adjusted safety margin being delivered, and switch to a minimum ventricular pacing mode and generating at least one of an alert and an observation of the determination of ineffective capture in response to effective CRT being less than the minimum effective CRT threshold.

Embodiment 8

The system of embodiment 7, wherein the processor is configured to determine whether a left ventricular capture management (LVCM) feature is enabled, generate an alert in response to the LVCM not being enabled, and adjust the safety margin in response to the LVCM feature being enabled.

Embodiment 9

The system of any of embodiments 1-8, wherein adjusting the safety margin comprises adjusting the safety margin from a baseline safety margin to an adjusted safety margin and adjusting the LV pre-excitation comprises adjusting the LV pre-excitation from a baseline LV pre-excitation to an adjusted LV pre-excitation, and the processor is configured to determine whether ineffective capture is resolved in response to the CRT pacing having the adjusted LV pre-excitation being delivered, adjust the LV pre-excitation from the adjusted LV pre-excitation to the baseline LV pre-excitation in response to determining ineffective capture as not being resolved in response to the CRT pacing having the adjusted LV pre-excitation being delivered, determine whether a vector adjustment feature associated with adjusting a vector for delivering the CRT pacing has been enabled in response to ineffective capture not being resolved in response to the CRT pacing having the adjusted LV pre-excitation being delivered, adjust the vector for delivering the CRT pacing in response to the vector adjustment feature being determined to be enabled, determine whether ineffective capture is resolved in response to the CRT pacing having the adjusted vector being delivered, determine whether ineffective capture is resolved in response to the CRT pacing having the adjusted safety margin being delivered, adjust the safety margin from the adjusted safety margin to the baseline safety margin in response to ineffective capture not being resolved in response to the CRT pacing having the adjusted safety margin being delivered, determine whether effective CRT is less than a minimum effective CRT threshold in response to ineffective capture not being resolved in response to the CRT pacing having the adjusted safety margin being delivered, and switch to a minimum ventricular pacing mode and generating at least one of an alert and an observation of the determination of ineffective capture in response to effective CRT being less than the minimum effective CRT threshold.

Embodiment 10

The system of embodiment 9, wherein the processor is configured to determine whether effective CRT is less than the minimum effective CRT threshold in response to the vector adjustment feature not being enabled, and switch to a minimum ventricular pacing mode and generating at least one of an alert and an observation of the determination of ineffective capture in response to effective CRT being less than the minimum effective CRT threshold.

Embodiment 11

The system of embodiment 10, wherein the processor is configured to determine whether a left ventricular capture management (LVCM) feature is enabled, generate an alert in response to the LVCM not being enabled, and adjust the safety margin in response to the LVCM feature being enabled.

Embodiment 12

A method of delivering cardiac resynchronization therapy (CRT) pacing, comprising: determining capture associated with the delivered CRT pacing is ineffective in response to the delivered CRT pacing; determining a reason for capture being ineffective; and adjusting one of a safety margin and a capture threshold in response to the determined reason for capture being ineffective being loss of capture and adjusting a left ventricle (LV) pre-excitation in response to the determined reason for capture being ineffective being delayed LV depolarization.

Embodiment 13

The method of embodiment 12, further comprising: determining whether a left ventricular capture management (LVCM) feature is enabled; generating an alert in response to the LVCM not being enabled; and adjusting the one of the safety margin and the capture threshold in response to the LVCM feature being enabled.

Embodiment 14

The method of any of embodiments 12 and 13, further comprising: determining whether a change in effective CRT occurs in response to the CRT pacing being delivered subsequent to performing one of adjusting of the one of the safety margin and the capture threshold and adjusting of the LV pre-excitation; determining ineffective capture as being resolved in response to the change in effective CRT being determined to occur; and determining ineffective capture as not being resolved in response to the change in effective CRT not being determined to occur.

Embodiment 15

The method of any of embodiments 12-14, further comprising: adjusting the LV pre-excitation from a baseline LV pre-excitation to an adjusted LV pre-excitation; determining whether ineffective capture is resolved in response to the CRT pacing having the adjusted LV pre-excitation being delivered; adjusting the LV pre-excitation from the adjusted LV pre-excitation to the baseline LV pre-excitation in response to determining ineffective capture as not being resolved; determining whether a vector adjustment feature associated with adjusting a vector for delivering the CRT pacing has been enabled in response to ineffective capture being determined as not being resolved; and adjusting the vector for delivering the CRT pacing in response to the vector adjustment feature being determined to be enabled.

Embodiment 16

The method of embodiment 15, further comprising: determining whether ineffective CRT is less than a minimum effective CRT threshold in response to the vector adjustment feature being determined to be not enabled; and switching to a minimum ventricular pacing mode and generating at least one of an alert and an observation of the determination of ineffective capture in response to effective CRT being less than the minimum effective CRT threshold.

Embodiment 17

The method of embodiment 15, further comprising: determining whether ineffective capture is resolved in response to the CRT pacing having the adjusted vector being delivered; determining whether effective CRT is less than a minimum effective CRT threshold in response to ineffective capture not being resolved in response to the CRT pacing having the adjusted vector being delivered; and switching to a minimum ventricular pacing mode and generating at least one of an alert and an observation of the determination of ineffective capture in response to effective CRT being less than the minimum effective CRT threshold.

Embodiment 18

The method of any of embodiments 12-17, further comprising: adjusting the safety margin from a baseline safety margin to an adjusted safety margin; determining whether ineffective capture is resolved in response to the CRT pacing having the adjusted safety margin being delivered; adjusting the safety margin from the adjusted safety margin to the baseline safety margin in response to determining ineffective capture as not being resolved; determining whether effective CRT is less than a minimum effective CRT threshold in response to ineffective capture not being resolved in response to the CRT pacing having the adjusted safety margin being delivered; and switching to a minimum ventricular pacing mode and generating at least one of an alert and an observation of the determination of ineffective capture in response to effective CRT being less than the minimum effective CRT threshold.

Embodiment 19

The method of embodiment 18, further comprising: determining whether a left ventricular capture management (LVCM) feature is enabled; generating an alert in response to the LVCM not being enabled; and adjusting the safety margin in response to the LVCM feature being enabled.

Embodiment 20

The method of any of embodiment 12, wherein adjusting the safety margin comprises adjusting the safety margin from a baseline safety margin to an adjusted safety margin and adjusting the LV pre-excitation comprises adjusting the LV pre-excitation from a baseline LV pre-excitation to an adjusted LV pre-excitation, the method further comprising: determining whether ineffective capture is resolved in response to the CRT pacing having the adjusted LV pre-excitation being delivered; adjusting the LV pre-excitation from the adjusted LV pre-excitation to the baseline LV pre-excitation in response to determining ineffective capture as not being resolved in response to the CRT pacing having the adjusted LV pre-excitation being delivered; determining whether a vector adjustment feature associated with adjusting a vector for delivering the CRT pacing has been enabled in response to ineffective capture not being resolved in response to the CRT pacing having the adjusted LV pre-excitation being delivered; adjusting the vector for delivering the CRT pacing in response to the vector adjustment feature being determined to be enabled; determining whether ineffective capture is resolved in response to the CRT pacing having the adjusted vector being delivered; determining whether ineffective capture is resolved in response to the CRT pacing having the adjusted safety margin being delivered; adjusting the safety margin from the adjusted safety margin to the baseline safety margin in response to ineffective capture not being resolved in response to the CRT pacing having the adjusted safety margin being delivered; determining whether effective CRT is less than a minimum effective CRT threshold in response to ineffective capture not being resolved in response to the CRT pacing having the adjusted safety margin being delivered; and switching to a minimum ventricular pacing mode and generating at least one of an alert and an observation of the determination of ineffective capture in response to effective CRT being less than the minimum effective CRT threshold.

Embodiment 21

The method of embodiment 20, further comprising: determining whether effective CRT is less than the minimum effective CRT threshold in response to the vector adjustment feature not being enabled; and switching to a minimum ventricular pacing mode and generating at least one of an alert and an observation of the determination of ineffective capture in response to effective CRT being less than the minimum effective CRT threshold.

Embodiment 22

The method of any of embodiments 20 and 21, further comprising: determining whether a left ventricular capture management (LVCM) feature is enabled; generating an alert in response to the LVCM not being enabled; and increasing the safety margin in response to the LVCM feature being enabled.

Embodiment 23

A non-transitory computer readable medium storing instructions which cause an implantable medical device to perform a method, the method comprising: determining capture associated with the delivered CRT pacing is ineffective in response to the delivered CRT pacing; determining a reason for capture being ineffective; and adjusting one of a safety margin and a capture threshold in response to the determined reason for capture being ineffective being loss of capture and adjusting a left ventricle (LV) pre-excitation in response to the determined reason for capture being ineffective being delayed LV depolarization.

What is claimed:

1. An implantable medical device system for delivering cardiac resynchronization therapy (CRT) pacing, comprising:
   an implantable medical device housing;
   at least one lead having a lead body and capable of being electrically coupled to the housing;
   a plurality of electrodes positioned along one or both of the device housing and the lead body of the at least one lead to sense a cardiac signal of the patient and to deliver the CRT pacing; and
   a processor positioned within the housing and configured to:
   determine capture associated with the delivered CRT pacing is ineffective in response to the delivered CRT pacing;
   determine loss of capture being a reason for ineffective capture;
   in response to loss of capture being determined, adjust one of a safety margin and a capture threshold;
   determine delayed left ventricle (LV) depolarization being a reason for ineffective capture; and
   in response to delayed LV depolarization being determined, adjust LV pre-excitation by modifying a VV delay of the CRT pacing, wherein the VV delay is a time period between a left ventricular pace and a right ventricular event of the CRT pacing.

2. The system of claim 1, wherein the processor is configured to determine whether a left ventricular capture management (LVCM) feature is enabled, generate an alert in response to the LVCM not being enabled, and adjust the one of the safety margin and the capture threshold in response to the LVCM feature being enabled.

3. The system of claim 1, wherein the processor is configured to determine whether a change in effective CRT occurs in response to the CRT pacing being delivered subsequent to performing one of adjusting of the one of the safety margin and the capture threshold and adjusting of the LV pre-excitation, determine ineffective capture as being resolved in response to the change in effective CRT being determined to occur, and determine ineffective capture as not being resolved in response to the change in effective CRT not being determined to occur.

4. The system of claim 1, wherein the processor is configured to adjust the LV pre-excitation from a baseline LV pre-excitation to an adjusted LV pre-excitation, determine whether ineffective capture is resolved in response to the CRT pacing having the adjusted LV pre-excitation being delivered, adjust the LV pre-excitation from the adjusted LV pre-excitation to the baseline LV pre-excitation in response to determining ineffective capture as not being resolved, determine whether a vector adjustment feature associated with adjusting a vector for delivering the CRT pacing has been enabled in response to ineffective capture being determined as not being resolved, and adjust the vector for delivering the CRT pacing in response to the vector adjustment feature being determined to be enabled.

5. The system of claim 4, wherein the processor is configured to determine whether ineffective CRT is less than a minimum effective CRT threshold in response to the vector adjustment feature being determined to be not enabled, and switch to a minimum ventricular pacing mode and generating at least one of an alert and an observation of the determination of ineffective capture in response to effective CRT being less than the minimum effective CRT threshold.

6. The system of claim 4, wherein the processor is configured to determine whether ineffective capture is resolved in response to the CRT pacing having the adjusted vector being delivered, determine whether effective CRT is less than a minimum effective CRT threshold in response to ineffective capture not being resolved in response to the CRT pacing having the adjusted vector being delivered, and switch to a minimum ventricular pacing mode and generating at least one of an alert and an observation of the determination of ineffective capture in response to effective CRT being less than the minimum effective CRT threshold.

7. The system of claim 1, wherein the processor is configured to adjust the safety margin from a baseline safety margin to an adjusted safety margin, determine whether ineffective capture is resolved in response to the CRT pacing having the adjusted safety margin being delivered, adjust the safety margin from the adjusted safety margin to the baseline safety margin in response to determining ineffective capture as not being resolved, determine whether effective CRT is less than a minimum effective CRT threshold in response to ineffective capture not being resolved in response to the CRT pacing having the adjusted safety margin being delivered, and switch to a minimum ventricular pacing mode and generating at least one of an alert and an observation of the determination of ineffective capture in response to effective CRT being less than the minimum effective CRT threshold.

8. The system of claim 7, wherein the processor is configured to determine whether a left ventricular capture management (LVCM) feature is enabled, generate an alert in response to the LVCM not being enabled, and adjust the safety margin in response to the LVCM feature being enabled.

9. The system of claim 1, wherein adjusting the safety margin comprises adjusting the safety margin from a baseline safety margin to an adjusted safety margin and adjusting the LV pre-excitation comprises adjusting the LV pre-excitation from a baseline LV pre-excitation to an adjusted LV pre-excitation, and the processor is configured to determine whether ineffective capture is resolved in response to the CRT pacing having the adjusted LV pre-excitation being delivered, adjust the LV pre-excitation from the adjusted LV pre-excitation to the baseline LV pre-excitation in response to determining ineffective capture as not being resolved in response to the CRT pacing having the adjusted LV pre-excitation being delivered, determine whether a vector adjustment feature associated with adjusting a vector for delivering the CRT pacing has been enabled in response to ineffective capture not being resolved in response to the CRT pacing having the adjusted LV pre-excitation being delivered, adjust the vector for delivering the CRT pacing in response to the vector adjustment feature being determined to be enabled, determine whether ineffective capture is resolved in response to the CRT pacing having the adjusted vector being delivered, determine whether ineffective capture is resolved in response to the CRT pacing having the adjusted safety margin being delivered, adjust the safety margin from the adjusted safety margin to the baseline safety margin in response to ineffective capture not being resolved in response to the CRT pacing having the adjusted safety margin being delivered, determine whether effective CRT is less than a minimum effective CRT threshold in response to ineffective capture not being resolved in response to the CRT pacing having the adjusted safety margin being delivered, and switch to a minimum ventricular pacing mode and generating at least one of an alert and an observation of the determination of ineffective capture in response to effective CRT being less than the minimum effective CRT threshold.

10. The system of claim 9, wherein the processor is configured to determine whether effective CRT is less than the minimum effective CRT threshold in response to the vector adjustment feature not being enabled, and switch to a minimum ventricular pacing mode and generating at least one of an alert and an observation of the determination of ineffective capture in response to effective CRT being less than the minimum effective CRT threshold.

11. The system of claim 10, wherein the processor is configured to determine whether a left ventricular capture management (LVCM) feature is enabled, generate an alert in response to the LVCM not being enabled, and adjust the safety margin in response to the LVCM feature being enabled.

12. A method of delivering cardiac resynchronization therapy (CRT) pacing, comprising:
determining capture associated with the delivered CRT pacing is ineffective in response to the delivered CRT pacing;
determining loss of capture being a reason for ineffective capture;
in response to loss of capture being determined, adjusting one of a safety margin and a capture threshold;
determining delayed left ventricle (LV) depolarization being a reason for ineffective capture; and
in response to delayed LV depolarization being determined, adjusting LV pre-excitation by modifying a VV delay of the CRT pacing, wherein the VV delay is a time period between a left ventricular pace and a right ventricular event of the CRT pacing.

13. The method of claim 12, further comprising:
determining whether a left ventricular capture management (LVCM) feature is enabled;
generating an alert in response to the LVCM not being enabled; and
adjusting the one of the safety margin and the capture threshold in response to the LVCM feature being enabled.

14. The method of claim 12, further comprising:
determining whether a change in effective CRT occurs in response to the CRT pacing being delivered subsequent to performing one of adjusting of the one of the safety margin and the capture threshold and adjusting of the LV pre-excitation;
determining ineffective capture as being resolved in response to the change in effective CRT being determined to occur; and
determining ineffective capture as not being resolved in response to the change in effective CRT not being determined to occur.

15. The method of claim 12, further comprising:
adjusting the LV pre-excitation from a baseline LV pre-excitation to an adjusted LV pre-excitation;
determining whether ineffective capture is resolved in response to the CRT pacing having the adjusted LV pre-excitation being delivered;
adjusting the LV pre-excitation from the adjusted LV pre-excitation to the baseline LV pre-excitation in response to determining ineffective capture as not being resolved;
determining whether a vector adjustment feature associated with adjusting a vector for delivering the CRT pacing has been enabled in response to ineffective capture being determined as not being resolved; and
adjusting the vector for delivering the CRT pacing in response to the vector adjustment feature being determined to be enabled.

16. The method of claim 15, further comprising:
determining whether ineffective CRT is less than a minimum effective CRT threshold in response to the vector adjustment feature being determined to be not enabled; and
switching to a minimum ventricular pacing mode and generating at least one of an alert and an observation of the determination of ineffective capture in response to effective CRT being less than the minimum effective CRT threshold.

17. The method of claim 15, further comprising:
determining whether ineffective capture is resolved in response to the CRT pacing having the adjusted vector being delivered;
determining whether effective CRT is less than a minimum effective CRT threshold in response to ineffective capture not being resolved in response to the CRT pacing having the adjusted vector being delivered; and
switching to a minimum ventricular pacing mode and generating at least one of an alert and an observation of the determination of ineffective capture in response to effective CRT being less than the minimum effective CRT threshold.

18. The method of claim 12, further comprising:
adjusting the safety margin from a baseline safety margin to an adjusted safety margin;
determining whether ineffective capture is resolved in response to the CRT pacing having the adjusted safety margin being delivered;
adjusting the safety margin from the adjusted safety margin to the baseline safety margin in response to determining ineffective capture as not being resolved;
determining whether effective CRT is less than a minimum effective CRT threshold in response to ineffective capture not being resolved in response to the CRT pacing having the adjusted safety margin being delivered; and switching to a minimum ventricular pacing mode and generating at least one of an alert and an observation of the determination of ineffective capture in response to effective CRT being less than the minimum effective CRT threshold.

19. The method of claim 18, further comprising:
determining whether a left ventricular capture management (LVCM) feature is enabled;
generating an alert in response to the LVCM not being enabled; and
adjusting the safety margin in response to the LVCM feature being enabled.

20. The method of claim 12, wherein adjusting the safety margin comprises adjusting the safety margin from a baseline safety margin to an adjusted safety margin and adjusting the LV pre-excitation comprises adjusting the LV pre-excitation from a baseline LV pre-excitation to an adjusted LV pre-excitation, the method further comprising:
determining whether ineffective capture is resolved in response to the CRT pacing having the adjusted LV pre-excitation being delivered;
adjusting the LV pre-excitation from the adjusted LV pre-excitation to the baseline LV pre-excitation in response to determining ineffective capture as not being resolved in response to the CRT pacing having the adjusted LV pre-excitation being delivered;
determining whether a vector adjustment feature associated with adjusting a vector for delivering the CRT pacing has been enabled in response to ineffective capture not being resolved in response to the CRT pacing having the adjusted LV pre-excitation being delivered;
adjusting the vector for delivering the CRT pacing in response to the vector adjustment feature being determined to be enabled;
determining whether ineffective capture is resolved in response to the CRT pacing having the adjusted vector being delivered;
determining whether ineffective capture is resolved in response to the CRT pacing having determining whether ineffective capture is resolved in response to the CRT pacing having the adjusted safety margin being delivered;
adjusting the safety margin from the adjusted safety margin to the baseline safety margin in response to ineffective capture not being resolved in response to the CRT pacing having the adjusted safety margin being delivered;
determining whether effective CRT is less than a minimum effective CRT threshold in response to ineffective capture not being resolved in response to the CRT pacing having the adjusted safety margin being delivered; and
switching to a minimum ventricular pacing mode and generating at least one of an alert and an observation of the determination of ineffective capture in response to effective CRT being less than the minimum effective CRT threshold.

21. The method of claim 20, further comprising:
determining whether effective CRT is less than the minimum effective CRT threshold in response to the vector adjustment feature not being enabled; and
switching to a minimum ventricular pacing mode and generating at least one of an alert and an observation of the determination of ineffective capture in response to effective CRT being less than the minimum effective CRT threshold.

22. The method of claim 21, further comprising:
determining whether a left ventricular capture management (LVCM) feature is enabled;
generating an alert in response to the LVCM not being enabled; and
increasing the safety margin in response to the LVCM feature being enabled.

23. A non-transitory computer readable medium storing instructions which cause an implantable medical device to perform a method, the method comprising:
determining capture associated with the delivered CRT pacing is ineffective in response to the delivered CRT pacing;
determining loss of capture being a reason for ineffective capture;
in response to loss of capture being determined, adjusting one of a safety margin and a capture threshold;
determining delayed left ventricle (LV) depolarization being a reason for ineffective capture and
in response to delayed LV depolarization being determined, adjusting LV pre-excitation by modifying a VV delay of the CRT pacing, wherein the VV delay is a time period between a left ventricular pace and a right ventricular event of the CRT pacing.

* * * * *